(12) United States Patent
Lacy et al.

(10) Patent No.: US 12,290,661 B2
(45) Date of Patent: May 6, 2025

(54) INFUSION PUMP

(71) Applicant: Danby Medical Ltd, London (GB)

(72) Inventors: Graham Lacy, London (GB); John Danby, Wakes Colne (GB); Stefan Taal, London (GB); Hugo Revellat, London (GB); Vasilios Kanellopoulos, Geneva (CH); Karsten Fischer, London (GB); Thomas Lacy, London (GB)

(73) Assignee: Danby Medical Ltd., London (GB)

( * ) Notice: Subject to any disclaimer, the term of this patent is extended or adjusted under 35 U.S.C. 154(b) by 913 days.

(21) Appl. No.: 17/433,097

(22) PCT Filed: Feb. 20, 2020

(86) PCT No.: PCT/EP2020/054544
§ 371 (c)(1),
(2) Date: Aug. 23, 2021

(87) PCT Pub. No.: WO2020/169769
PCT Pub. Date: Aug. 27, 2020

(65) Prior Publication Data
US 2022/0096736 A1     Mar. 31, 2022

(30) Foreign Application Priority Data

Feb. 22, 2019   (GB) ....................... 1902414

(51) Int. Cl.
*A61M 5/145*    (2006.01)
*A61M 5/168*    (2006.01)
(Continued)

(52) U.S. Cl.
CPC ...... *A61M 5/1454* (2013.01); *A61M 5/16881* (2013.01); *A61M 5/14546* (2013.01);
(Continued)

(58) Field of Classification Search
CPC .............. A61M 5/1454; A61M 5/1688; A61M 2205/332; A61M 5/142; A61M 5/14566;
(Continued)

(56) References Cited

U.S. PATENT DOCUMENTS 4,668,220 A * 5/1987 Hawrylenko ....... A61M 5/1454
                                              604/209
4,741,736 A    5/1988 Brown
(Continued)

FOREIGN PATENT DOCUMENTS

EP          3335745 A1    6/2018
WO          201312742 A1  9/2013
WO          2016196102 A1 12/2016

*Primary Examiner* — William R Carpenter
*Assistant Examiner* — Robert F Allen (57) ABSTRACT

An infusion pump for administering controlled doses of fluid comprises a pump body 2 and cap 3 attachable to the pump body 2 to retain a medicament fluid receptacle 4 in the pump body 2. The fluid receptacle 4 is connected to a tube 12 for dispensing the fluid. The tube 12 is directed through a normally closed valve within the cap 3. The pump body 2 comprises a propulsion device engaging with a piston support 6 of the fluid receptacle 4, coupled to a retaining member, a drive system coupled to the retaining member and a rigid member coupled to the drive system. Actuation of the drive system enables the propulsion device to deliver fluid. In addition, the rigid member moveably projects into the cap to open the normally closed valve to allow the passage of fluid.

20 Claims, 9 Drawing Sheets

(51) Int. Cl.
  *A61M 39/10* (2006.01)
  *A61M 39/24* (2006.01)
(52) U.S. Cl.
  CPC ....... *A61M 5/1456* (2013.01); *A61M 5/14566* (2013.01); *A61M 2039/1027* (2013.01); *A61M 2039/2473* (2013.01); *A61M 2205/12* (2013.01); *A61M 2205/332* (2013.01)
(58) Field of Classification Search
  CPC ................ A61M 39/26; A61M 39/281; A61M 5/14546; A61M 5/1456; A61M 2039/2473; A61M 2205/12; A61M 2039/1027
  See application file for complete search history.

(56) References Cited

U.S. PATENT DOCUMENTS

| | | | | |
|---|---|---|---|---|
| 9,339,607 | B2* | 5/2016 | Langley | A61M 5/31511 |
| 2004/0092873 | A1* | 5/2004 | Moberg | A61M 39/12 |
| | | | | 604/126 |
| 2011/0028897 | A1* | 2/2011 | Swan | A61M 5/1454 |
| | | | | 604/151 |
| 2011/0208123 | A1* | 8/2011 | Gray | H01M 50/213 |
| | | | | 604/151 |
| 2014/0249412 | A1* | 9/2014 | Yamamoto | A61M 5/14546 |
| | | | | 600/432 |
| 2014/0288423 | A1* | 9/2014 | Yamamoto | A61M 5/007 |
| | | | | 600/432 |
| 2015/0018779 | A1* | 1/2015 | Nzike | F16F 3/04 |
| | | | | 267/168 |
| 2015/0057613 | A1* | 2/2015 | Clemente | A61M 5/14566 |
| | | | | 604/244 |
| 2017/0354782 | A1 | 12/2017 | Quinn et al. | |
| 2018/0085517 | A1* | 3/2018 | Laurence | A61M 5/14216 |

\* cited by examiner

INFUSION PUMP

The present invention relates to an infusion pump for administering controlled doses of fluid and in particular to an ambulatory infusion pump for administering medicament fluid to a patient. The infusion pump comprises means to ensure the efficacious delivery of the medicament fluid and means to ensure safe use of the infusion pump in the event of breakage and in the event of incorrect use.

Infusion of controlled flows or volumes of medicament fluid over a controlled and often long period of time are advantageous to many treatments when the body must receive gradual amounts of medicament and not a dose in a single event. They can also be advantageous when the flow of medicament fluid is to be increased or reduced in response to the observed or measured condition of the patient. Such infusion pumps may be connected to a patient for considerable periods of time during which the patient might be healthy and mobile and so the ambulatory nature of the infusion pump provides convenience and discretion.

BACKGROUND

Many ambulatory infusion pumps share technology with similar devices that are powered by mains electricity and even when such pumps are powered by portable electrical cells they can be physically large and heavy making their portability inconvenient and their concealment impractical.

Several devices are known that use stored mechanical energy referred to as potential energy as an alternative to electrical cells in attempts to reduce size, weight and the complexity of an infusion pump. These devices might use several different types of receptacle for the medicament fluid.

The following use cylindrical syringe receptacles:

U.S. Pat. No. 3,797,488 A describes an Ampoule Applicator whereby a spring provides the force applying means to provide pressure to deliver fluid from the Ampoule. An arrangement at the end of the spring nearest the fluid outlet is retained by a cable which is released by a lever to deliver the fluid. A clutch in between the spring and the fluid uses a ball bearing to create a wedge action against the interior walls providing a safety device at full stroke if the Ampoule is not present to prevent further forward motion of the spring. In the invention described in U.S. Pat. No. 3,797,488 A the cable is not controlled during fluid delivery to regulate the fluid flow and the safety device does not act in the event of cable breakage. The flow of fluid in the invention of U.S. Pat. No. 3,797,488 A depends upon the variable force provided by the spring through its motion and reduces as the spring extends and its force diminishes.

GB 2166497 A describes an invention in which the motive force for fluid delivery is provided by a spring which is controllably released by a motor to control the flow of fluid. This motor rotates a lead-screw that engages with a non-rotating gear upon a rod connected to the end of the spring nearest the fluid outlet. GB 2166497 A thereby describes a mechanism that controls fluid flow but the arrangement requiring a long rod and leadscrew is not compact for the user.

WO 2004/024218 A1 describes an infusion pump comprising a reservoir for storing liquid agent and a drive mechanism for propelling a piston towards an outlet from the reservoir to discharge the agent. The drive mechanism permanently forces the piston forwards and a locking mechanism locks progress of the piston permanently. The locking mechanism is released by operation of an escapement mechanism under electronic control.

CA 2496587 A describes an infusion pump comprising a helical spring to provide the propulsion and holding means to retain the advancement of a piston. The locking mechanism described is in the form of discrete and alternately engaged teeth, known as escapement mechanisms and used in watchmaking. There are no means described to provide safety features in the event of a failure of the holding back means.

WO 2008/142394 A1 describes an arrangement comprising a receptacle for fluid, a plunger and a propulsion mechanism for the fluid. This invention uses a motor connected to a worm and a worm wheel mechanism that secures a retaining member connected to the plunger to control or prevent travel of the plunger affecting the rate at which fluid is expelled. This invention describes accurate control of the fluid expelled. WO 2008/142394 A1 also describes self-activated means that ensure that the fluid is not administered from the receptacle in the event of breakage of the retaining member. This is described as a brake mechanism which can be in the form of a spring with radial fingers the outer surfaces or corners of which engage with the inner wall of the receptacle.

SUMMARY OF THE INVENTION

According to an embodiment there is provided an infusion pump for controllably dispensing fluid. The infusion pump comprising: an infusion pump body configured to receive a receptacle of fluid; and a cap configured to receive a tube coupled to the fluid receptacle for dispensing the fluid, the cap comprising a valve configured to occlude the tube; the infusion pump body comprising: a propulsion device biased to propel fluid from the fluid receptacle into the tube; a retaining member coupled to the propulsion device; a drive system coupled to the retaining member, wherein actuation of the drive system enables the propulsion device to controllably dispense the fluid; and a rigid member coupled to the drive system and configured to moveably project into the cap to open the valve to allow the passage of fluid through the tube.

According to another embodiment, the valve comprises a fixed valve part and a moveable valve part.

According to another embodiment, the rigid member is configured to displace the moveable valve part away from the fixed valve part when the rigid member projects into the cap to allow the passage of fluid through the tube.

According to another embodiment, the valve further comprises a biasing member configured to bias the moveable valve part towards the fixed valve part to occlude the tube.

According to another embodiment, the biasing member is configured to expel the rigid member from the cap when all of the fluid has been propelled from the fluid receptacle.

According to another embodiment, the rigid member is configured to moveably project into the cap to prevent the cap from opening.

According to another embodiment, the rigid member is configured to moveably project into the cap to prevent removal of the cap from the infusion pump.

According to another embodiment, the retaining member comprises a plurality of retaining cables.

According to another embodiment, the infusion pump further comprises: a retaining helical spring surrounding the retaining member.

According to another embodiment, the retaining helical spring is configured to contract to its natural length when a fluid receptacle is inserted into the pump body.

According to another embodiment, the retaining helical spring is coupled at a first end to the propulsion device and is coupled at a second end to the pump body.

According to another embodiment, the infusion pump further comprises: a control system for controlling actuation of the drive system.

According to another embodiment, one of the cap or the infusion pump body further comprises a sliding member configured to moveably project into a cooperating cavity provided in the other of the cap or the infusion pump body.

According to another embodiment, the control system comprises a sensor configured to detect when the sliding member projects into the cooperating cavity.

According to another embodiment, the infusion pump body further comprises a moveable stop bar configured to prevent the propulsion means projecting beyond the infusion pump body when no fluid receptacle is provided in the infusion pump body.

According to another embodiment, when a fluid receptacle is provided in the infusion pump body, the drive system is further configured to provide tension in the retaining member enabling the rigid member to project into the cap.

According to another embodiment, the drive system comprises a motor and an encoder coupled to the motor, the encoder configured to determine a number of motor revolutions and/or fractions thereof required to provide the tension in the retaining member when a fluid receptacle is provided in the infusion pump body.

According to another embodiment, the drive system comprises a force sensor configured to measure the tension in the retaining member.

According to another embodiment, the drive system comprises a worm mounted on a shaft, and wherein the force sensor is provided at an end of the worm or on the shaft to measure axial force upon the worm.

According to another embodiment, the force sensor is provided within a part that is supporting the axial force from the end of the worm or the shaft.

According to another embodiment, the infusion pump body further comprises a braking member coupled to a moveable end of the propulsion device and the retaining member, the braking member configured to prevent the propulsion device from propelling fluid from the fluid receptacle into the tube when the tension is removed from the retaining member.

According to another embodiment, the braking member comprises flexing members configured to engage the fluid receptacle, wherein the flexing members provide a lower engagement force and a higher disengagement force.

According to another embodiment, the pump body and the cap comprise corresponding locking features configured to retain a fluid receptacle within the pump body of the infusion pump.

According to another embodiment, the propulsion device comprises a two or more concentrically arranged helical springs, adjacent springs having opposing directions of winding.

According to another embodiment, the two or more concentrically arranged helical springs are each longer in natural length than the length of the fluid receptacle by a factor equal to or greater than 1.5.

According to another embodiment, when a full fluid receptacle is provided in the infusion pump body, the two or more concentrically arranged helical springs are compressed, and the length available in the infusion pump body for the compressed two or more concentrically arranged helical springs is longer than a coil-bound length of the two or more concentrically arranged helical springs by a factor equal to or greater than 1.1.

According to another embodiment, a fixed end of the propulsion device is coupled to the pump body and a moveable end of the propulsion device is biased to move away from the fixed end of the propulsion device.

According to another embodiment, the retaining member extends through a center of the propulsion device.

According to another embodiment, the infusion pump body is configured to receive a fluid receptacle comprising connection features for connection to opposing connection features of a disengageable handle, wherein the connection features requires the handle or fluid receptacle to be rotated with a higher torque, than required to engage the handle to the fluid receptacle, so as to overcome the connection features and remove the handle.

BRIEF DESCRIPTION OF THE DRAWINGS

Examples will now be described by reference to the accompanying drawings.

DETAILED DESCRIPTION

Figure 1:
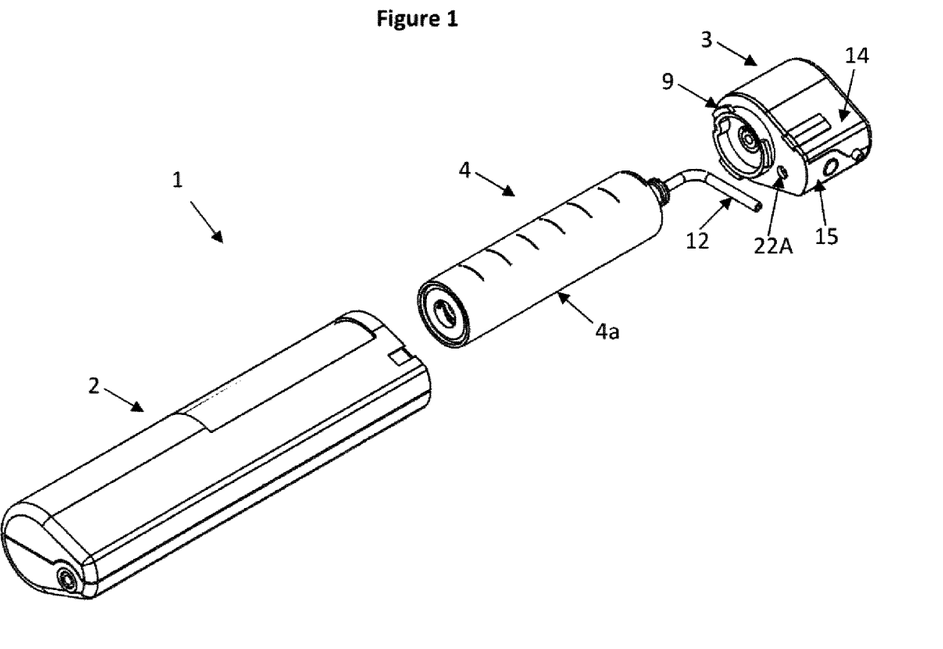
FIG. 1 illustrates an infusion pump disassembled into an infusion body and a cap, a fluid receptacle is also shown.
Figure 5:
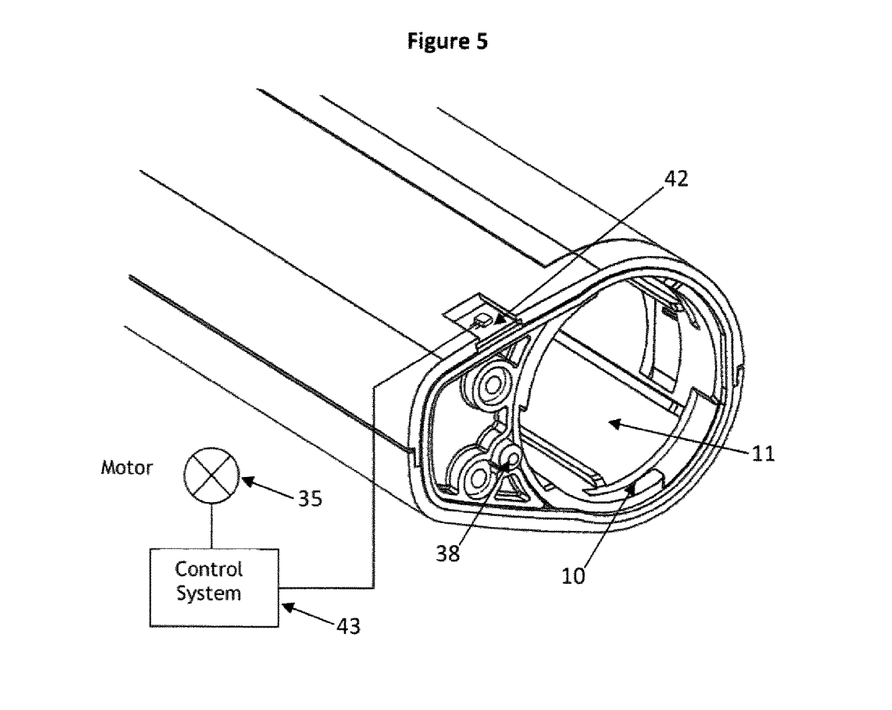
FIG. 5 illustrates a partial view of the outside of the pump body at the end to be fitted to the cap.

FIG. 1 schematically illustrates an infusion pump 1. The infusion pump 1 comprises an infusion body 2 and a cap 3. The cap 3 is provided with locking features 9 such as a bayonet, screw, catch or similar, to connect the cap 3 to the body 2 of the infusion pump 1. The body 2 of the infusion pump 1 is provided with corresponding locking features 10 such as a bayonet, screw, catch or similar, illustrated in FIG.

5. The infusion body 2 and the cap 3 are configured to retain a fluid receptacle 4 in a cavity volume 11 within the body 2 of the infusion pump 1.

Figure 3:
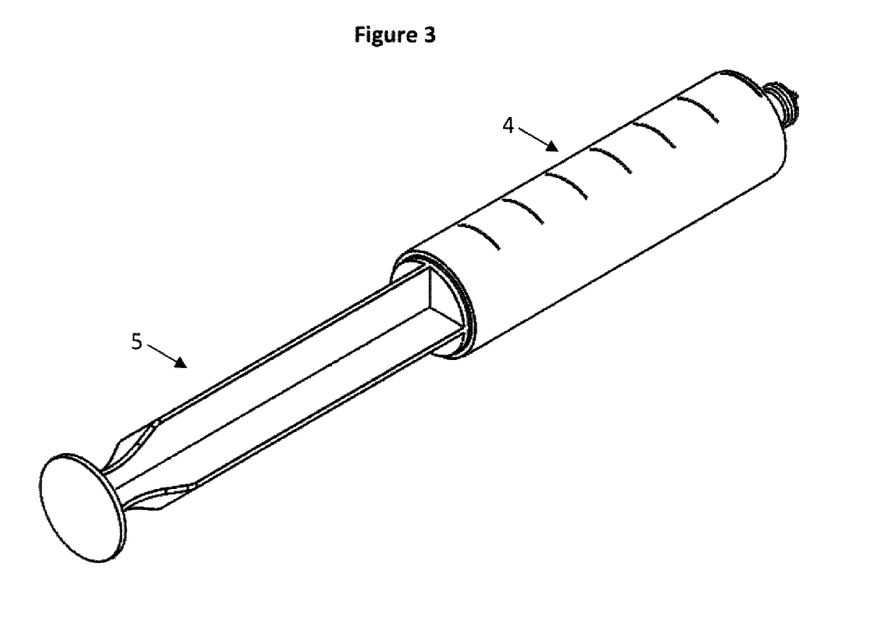
FIG. 3 illustrates an external view of a fluid receptacle with a handle.
Figure 4:
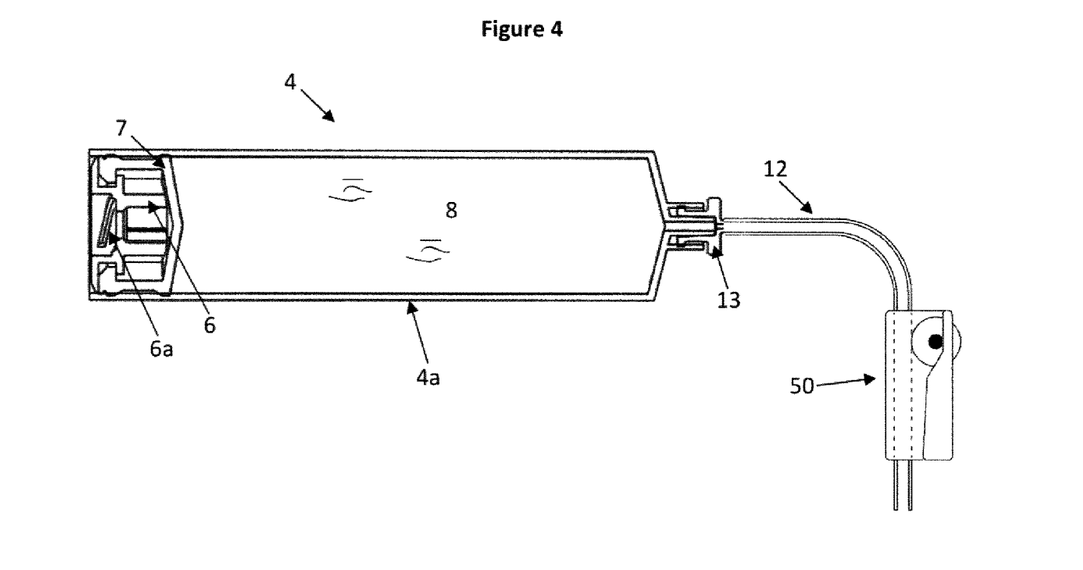
FIG. 4 illustrates a cross-sectional view of a fluid receptacle with a tube and a tube clamp.

FIGS. 3 and 4 illustrate embodiments of a fluid receptacle 4. The fluid receptacle 4 of FIGS. 3 and 4 comprises a cylindrical body 4a and a piston arrangement comprising a seal support 6 and seal 7. The seal support 6 and seal/piston 7 enable the introduction of medicament fluid 8 into the receptacle 4 and can be fitted to a handle 5 for the purpose of moving the piston arrangement. In addition, the seal support 6 and seal/piston 7 enable the expulsion of medicament fluid 8 from the receptacle 4 by the infusion pump 1, the seal support 6 being configured for connection to a propulsion device (described in further detail below) when the fluid receptacle 4 is provided within the body 2 of the infusion pump 1.

The seal support 6 within the fluid receptacle 4 may comprises connection features 6a such as a screw, bayonet or clips to interact with corresponding and opposing surfaces of the handle 5, such that the handle 5 may be engaged with and disengaged from the seal support 6. The handle 5, when engaged with the fluid receptacle 4 may be used by a user to draw the required volume of fluid into the fluid receptacle 4 through its open end. The handle 5 can then be disengaged from the seal support 6 for example by rotation leaving the seal support 6 and seal 7 in an unchanged position within the receptacle, such that the fluid receptacle comprising fluid may then be provided in an infusion pump.

The connection features of the handle 5 and the seal support 6 may interact by rotation. In order to disengage the handle 5 from the seal support 6 of the fluid receptacle 4, the connection features require the handle 5 or fluid receptacle 4 to be rotated with a higher torque, than required to engage the handle 5 to the seal support 6 of the fluid receptacle 4, so as to overcome the connection features before further rotation to remove the handle 5. Removal of the handle 5 make it possible for the propulsion device to extend inside the fluid receptacle resulting in a smaller infusion pump In an alternative embodiment, a prefilled fluid receptacle 4, similar to the fluid receptacle 4 described with reference to FIGS. 3 and 4 may be provided, the prefilled fluid receptacle 4 filled with the required volume of fluid. According to this embodiment, the prefilled fluid receptacle 4 may not comprise the connection features 6a for connection to the handle 5, since the prefilled fluid receptacle 4 is prefilled with the required volume of fluid, attachment to/from the handle 5 is not required.

The fluid receptacle 4/prefilled fluid receptacle 4 is configured to be connected by an operator nurse or patient to a tube 12. According to one embodiment, the fluid receptacle 4/prefilled fluid receptacle 4 may be connected to the tube 12 by means of an industry standard Luer connector 13. The tube 12 may include a clamp 50 of sliding or rolling design fitted within its length.

Figure 6:
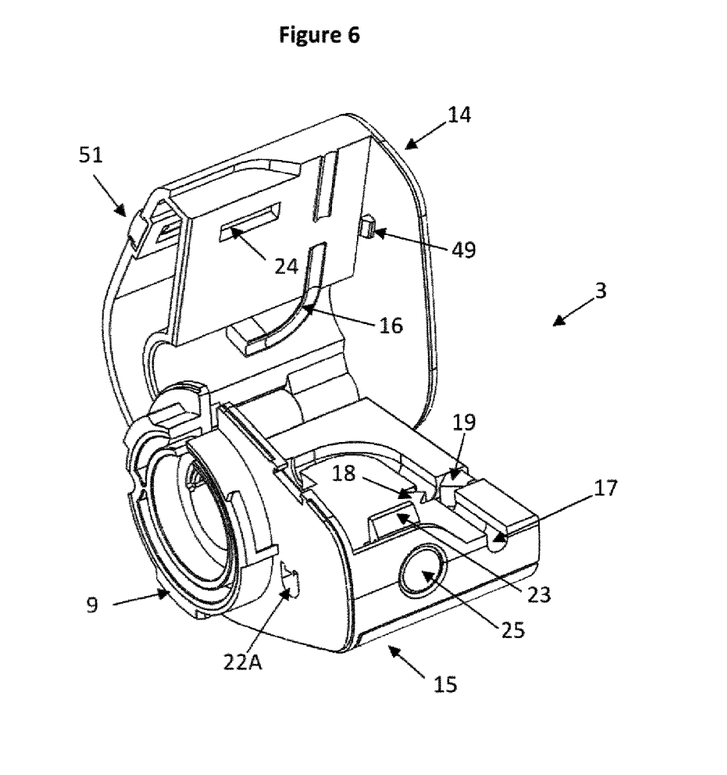
FIG. 6 illustrates a cap in an open state.
Figure 7:
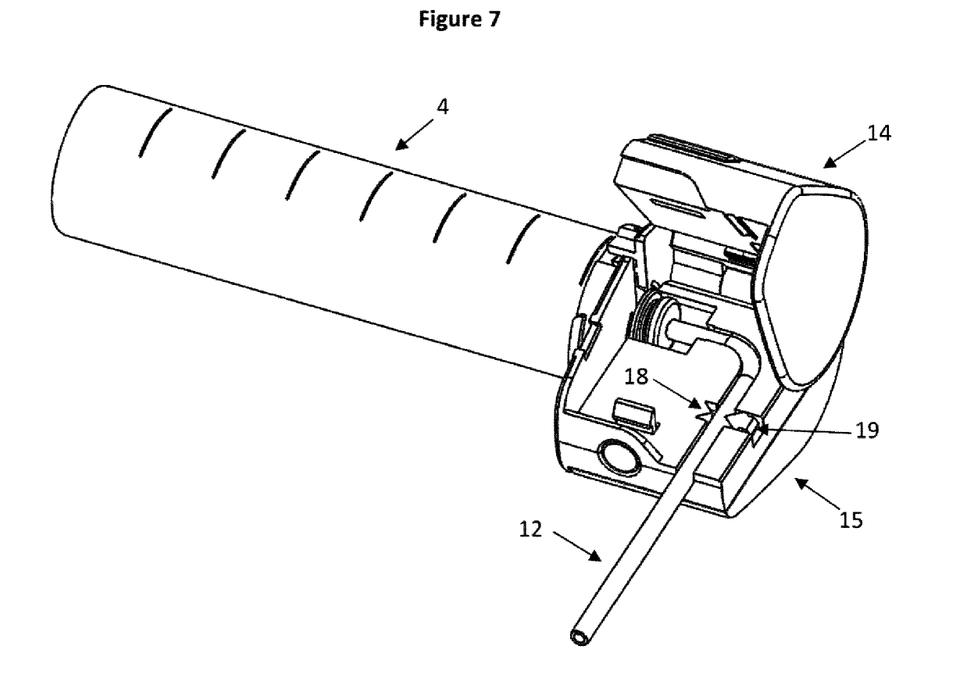
FIG. 7 illustrates a cap in an open state with a fluid receptacle and a tube fitted.

As illustrated in FIG. 6, the cap 3 comprises a lid part 14 connected to a base part 15. The lid 14 comprises features such as walls or ribs 16 that cooperate with features on the base 15 such as ribs or walls. In addition, the lid 14 and/or base 15 may comprise a channel 17 configured to receive the tube 12. The channel 17 ensures that the tube 12, when fitted into the cap 3, will be directed along a predetermined path and through a pinch valve as illustrated in FIG. 7. The pinch valve is configured to occlude the tube 12 and prevent the passage of fluid through the tube 12.

Figure 8:
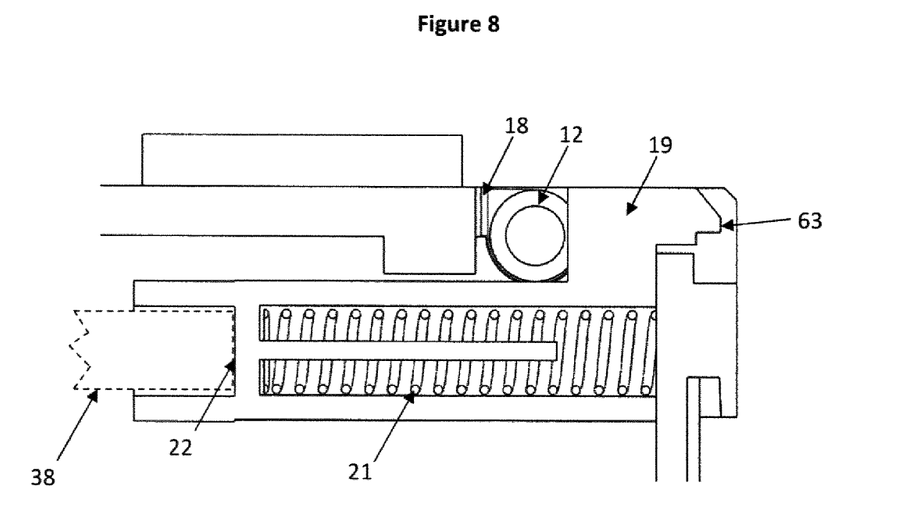
FIG. 8 illustrates a cross-sectional view of a pinch valve within the cap.

The pinch valve, illustrated in more detail in FIG. 8, comprises a fixed valve part 18 and a moveable valve part 19 within the base 15 for contact with the tube 12. Alternatively, the pinch valve may be provided in the lid 14 for contact with the tube 12. The fixed valve part 18 and moveable valve part 19 create cooperating and opposing contact surfaces which occlude the tube 12, when required, to prevent the passage of fluid through the tube 12. The pinch valve also comprises a biasing member such as a metal helical spring or rubber spring 21 to ensure that the pinch valve normally resides in a state that occludes the tube 12 when the tube 12 is present. The moveable valve part 19 comprises a cooperating surface 22 which may be acted upon by a rod tube or rigid member 38 of the infusion pump body 2, when the cap 3 is connected to the pump body 2 and a fluid receptacle 4 is provided within the body 2 of the infusion pump 1, for the purpose of compressing the biasing member 21 and displacing the moveable valve part 19 away from the tube 12 to allow the passage of fluid through the tube 12.

When the fluid receptacle 4 is connected to the cap 3 and the tube 12 positioned in the channel 17, as illustrated in FIG. 7, the pinch valve prevents the passage of fluid, whilst the fluid receptacle 4 is loaded into the body 2 of the infusion pump and the body 2 of the infusion pump is connected to the cap 3. Following insertion of the fluid receptacle 4 into the infusion pump 1 the pinch valve prevents the passage of fluid until the moveable valve part 19 is displaced away from the tube 12, as discussed in detail below.

Figure 17:
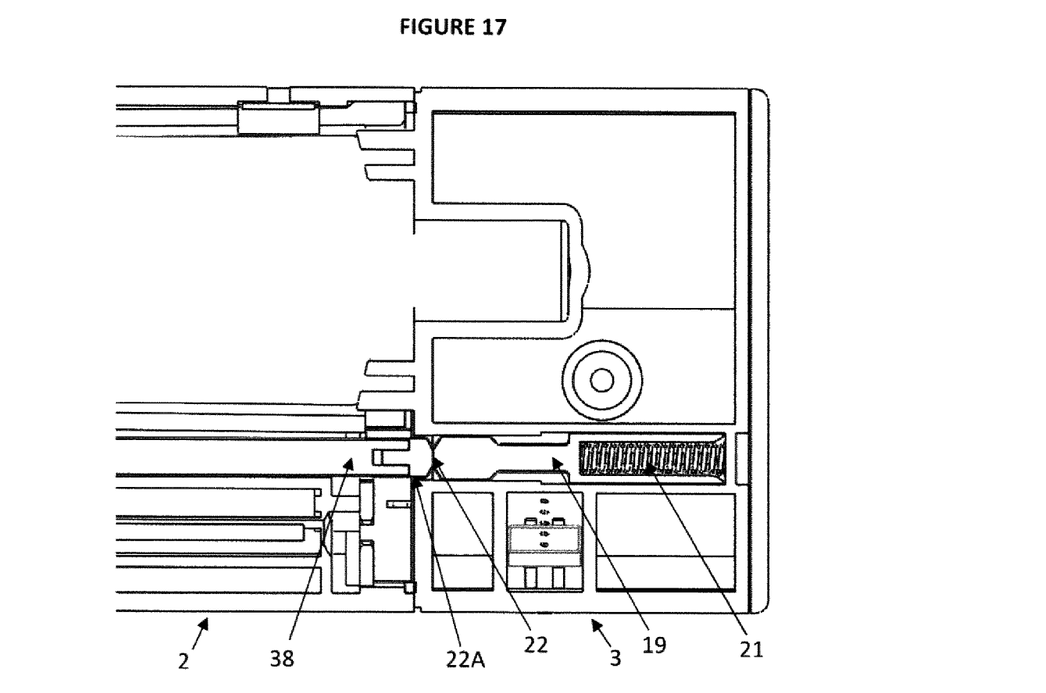
FIG. 17 illustrates a partial cross-sectional view of a pump body and cap arrangement.

When a fluid receptacle 4 is connected to the tube 12 and provided within the body 2 of the infusion pump 1, the rigid member 38 may project from the body 2 of the infusion pump 1 into the cap 3 through hole 22A illustrated in FIGS. 6 and 17. The rigid member 38 is configured to project into the cap 3 and to act on the cooperating surface 22 so as to displace the moveable valve part 19 away from the tube 12 and allow the passage of fluid through the tube 12 when a retaining member 31 of the pump body 2 becomes under tension. FIG. 17 illustrates the rigid member 38 projecting from the body 2 of the infusion pump 1 into the cap 3 and contacting the surface 22 to compress the biasing member 21. Consequently, fluid will only flow from the fluid receptacle 4 through the tube 12 to the patient when the infusion pump 1 has been connected to the cap 3 and is actuated to dispense fluid. This is advantageous in that the amount of medicament fluid 8 dispensed to the patient can be accurately monitored.

Furthermore, by virtue of the rigid member 38 projecting from the body 2 of the infusion pump 1 into the cap 3, the cap 3 cannot be removed from the infusion pump body 2 or opened whilst the infusion pump 1 is dispensing medicament. Consequently, the fluid receptacle 4 and thus the medicament cannot be removed from the infusion pump 1. This prevents the medicament fluid 8 from being tampered with or stolen during ambulatory infusion. This also removes the necessity for the infusion pump being provided in a further mechanical enclosure, commonly referred to as a lockbox, in order to prevent the medicament fluid 8 from being tampered with or stolen during ambulatory infusion.

Returning to FIG. 6, the cap 3 also comprises a catch feature 23 on the cap base 15 which engages with a corresponding ledge feature 24 on the lid 14 to retain the lid and base in a closed position once closed by a user. A button 25 is provided on the base 15. When the button 25 is depressed it disengages the catch feature 23 from the ledge feature 24 so that the cap 3 can then be opened. Although the catch feature 23 is illustrated on the cap base 15 and the ledge feature 24 is illustrated on the lid 14, the catch feature 23 may be provided on the lid 14 and the ledge feature 24 may be provided on the cap base 15. In addition, the button 25 may be provided on the base 15 or the lid 14.

Figure 10:
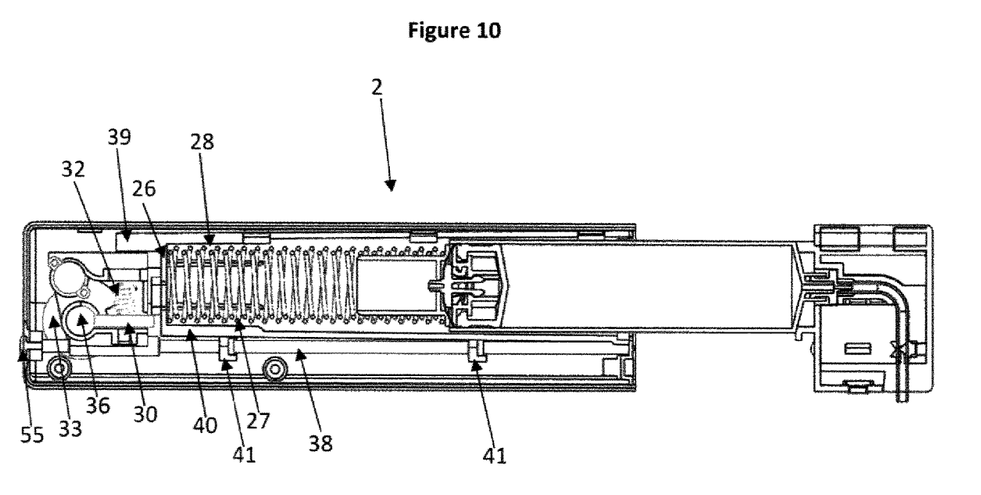
FIG. 10 illustrates a cross sectional view of an infusion pump with a fluid receptacle fitted.
Figure 14:
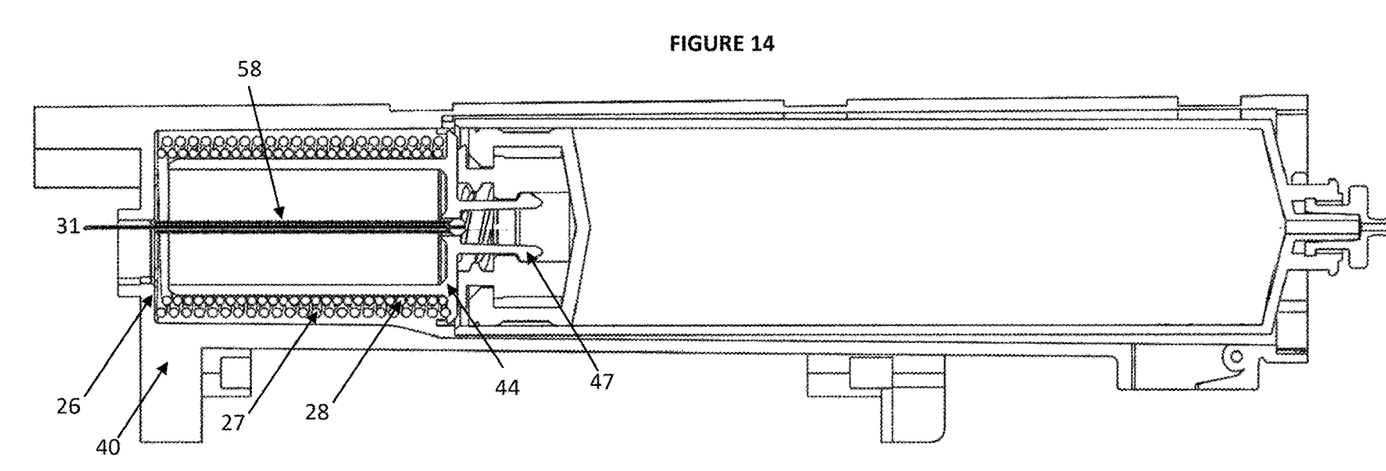
FIG. 14 illustrates a partial cross-sectional view of a pump body fitted with a full fluid receptacle.
Figure 15:
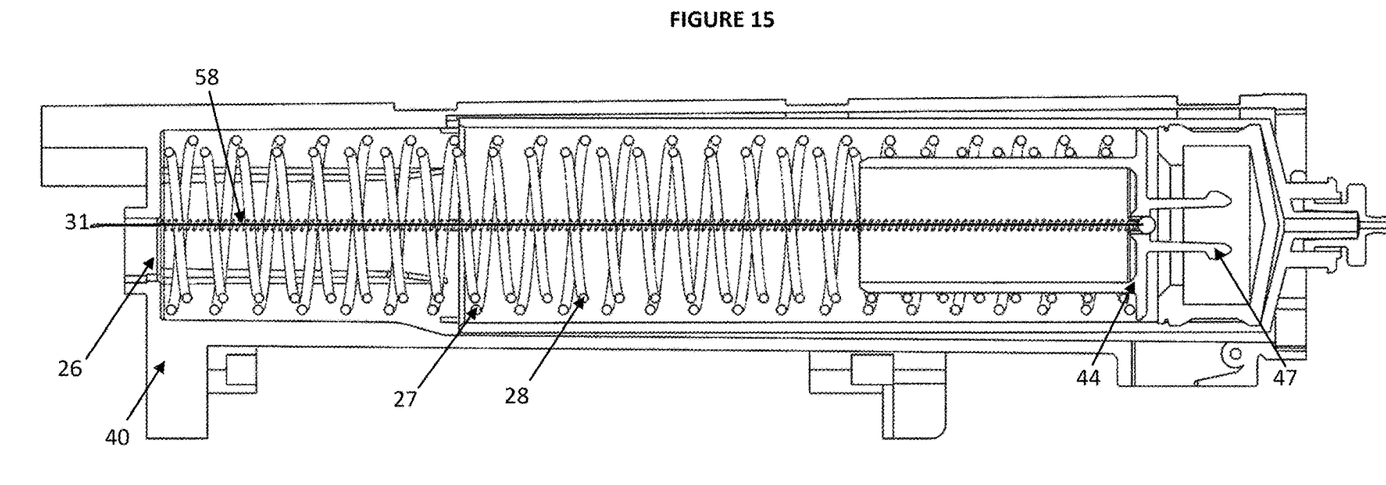
FIG. 15 illustrates a partial cross-sectional view of a pump body fitted with an empty fluid receptacle.

Referring to FIGS. 10, 14 and 15, the infusion pump body 2 comprises a propulsion device. When a fluid receptacle body 4 is provided in the body 2 of the infusion pump 1, the propulsion device is compressed such that it is biased to advance the piston 7 along the fluid receptacle body 4a and to propel medicament fluid 8 from the fluid receptacle 4 into the tube 12, consequently a patient to whom the infusion pump 1 is connected receives gradual amounts of medicament.

The propulsion device comprises a fixed end and a moveable end. The fixed end of the propulsion device is attached to a wall of the pump body 2. Preferably, the fixed end of the propulsion device is attached to an internal wall of the pump body 2, such as the internal chassis part 40. According to one embodiment, the fixed end of the propulsion device is attached to a perpendicular wall 26 of the internal chassis part 40.

The moveable end of the propulsion device is provided with a support 44. When a fluid receptacle 4 is provided within the body 2 of the infusion pump 1, then a connector, such as clips 47, of the support 44 engages with the seal support 6 of the fluid receptacle 4.

The propulsion device preferably comprises a plurality of concentrically arranged helical springs, adjacent springs having opposing directions of winding. However, the propulsion device may be any means capable of propelling fluid from the fluid receptacle 4 into the tube 12. The propulsion device illustrated in FIGS. 10, 11, 14 and 15 comprises two concentrically arranged helical springs, the two springs having opposing directions of winding when viewed from a common end, for example a clockwise wound outer spring 27 and an anticlockwise wound inner spring 28.

According to the disclosure herein, a plurality of helical springs means one or more helical springs. Consequently, the propulsion device may be provided with one, two, three, or more concentrically arranged helical springs.

When two or more springs are provided, the springs are arranged concentrically having alternating opposing directions of winding when viewed from a common end. For example, when three springs are provided, the outermost spring may comprise a clockwise wound spring, the middle spring may comprise an anticlockwise wound spring and the innermost spring may comprise a clockwise wound spring.

The plurality of springs have alternating opposing directions of winding so that the coils of one spring do not become trapped within the gaps of another adjacent spring or springs in such a way that they might obstruct compression of the springs or reduce the space between some of the successive coils.

It is preferable to a user that the infusion pump comprises a compact size. It has been found that one spring may not provide the required force over the required length for a compact infusion pump to propel medicament fluid from a fluid receptacle into the tube. The propulsion device may comprise two or more springs in order to provide the required force over the required length of the fluid receptacle 4. The appropriate number of springs may be provided depending on the force required and the size of the infusion pump 1 and the fluid receptacle 4. In addition, an infusion pump 1 comprising a plurality of springs is able to provide sufficient pressure throughout the emptying of the receptacle 4, such that the force provided by the springs remains sufficient as the springs extend. The infusion pump is also able to provide increased pressure, if required, to overcome obstructions within the tube or patient that would otherwise create backpressure that reduces the rate of passage of fluid.

Each spring of the propulsion device comprises a different diameter when viewed from a common end, such that the springs may be concentrically arranged. For example, when three springs are provided, the innermost spring may comprise a diameter x, the middle spring may comprise a diameter x+1 and the outermost spring may comprise a diameter x+2.

According to one embodiment, the plurality of helical springs may or may not be formed from the same material. The helical springs may be formed from metal, carbon or reinforced polymer. The thickness of the material which is coiled to form each helical spring may or may not be the same.

Each spring of the propulsion device may comprise the same number or a different number of windings. Preferably each spring of the propulsion device has the same or similar length.

It is preferable that the natural length of the propulsion device, being the length of the propulsion device when unloaded, i.e. neither compressed nor stretched, is considerably longer than the longest length in use determined by the length of the fluid receptacle 4. According to one embodiment, the natural length of the propulsion device is longer than the length of the fluid receptacle by a factor equal to or greater than 1.5. According to one embodiment, when a fluid receptacle 4 full of fluid is fitted in the cavity 11 within the pump body 2, the propulsion device is compressed. The remaining length available for the propulsion device, when the full fluid receptacle 4 is fitted in the cavity 11 exceeds the fully compressed length (coil-bound length) of the propulsion device by a factor equal to or greater than 1.1.

As illustrated in FIGS. 14 and 15, a retaining member 31 is connected at a first end to the support 44 and a second end of the retaining member 31 is connected to a drive system provided at the infusion pump body 2. According to the embodiment illustrated in FIGS. 14 and 15, the retaining member 31 extends through the center of the propulsion device.

The propulsion device is compressed when the moveable end of the propulsion device is moved towards the fixed end of the propulsion device, biasing the propulsion device. In use, the propulsion device is compressed when a fluid receptacle 4 is inserted into the infusion pump 1. The natural tendency of the propulsion device is to extend in length, i.e. to decompress. However, following insertion of a fluid receptacle 4 into the infusion pump 1, the retaining member 31 is provided under tension, by the drive system. The tension in the retaining member 31 acts against the natural tendency of the propulsion device to extend in length. The retaining member 31 together with the drive system exerts a force on the propulsion device, keeping the propulsion device in compression. The force may be released by actuation of the drive system. Consequently, the retaining member 31 and drive system prevent the propulsion device from decompressing more than a required amount over time and thus prevent the infusion pump from discharging more than the required amount of fluid in one go.

The retaining member 31 may comprise a plurality of retaining cables. According to the disclosure herein, a plurality of retaining cables means one or more retaining cables. The cables may comprise chains, stranded metal cables, monofibres or woven fibres such as carbon, Ultra-High Molecular Weight Polyethylene or Polyparaphenylene Terephthalamide or a combination thereof.

According to one embodiment, the retaining member 31 is surrounded by a retaining helical spring 58. The retaining helical spring 58 is connected at a first moveable end to the support 44 together with the retaining member 31. A second fixed end of the retaining helical spring 58 is attached to a wall of the pump body 2. Preferably, the second end of the retaining helical spring 58 is attached to an internal wall of the pump body 2, such as the internal chassis part 40. According to one embodiment, the second end of the retaining helical spring 58 is attached to a perpendicular wall 26 of the internal chassis part 40.

When the propulsion device is compressed within the infusion pump 1, as illustrated in FIG. 14, the retaining helical spring 58 is at or near to its natural length (i.e. neither compressed nor stretched). However, when the propulsion device is fully extended within the infusion pump 1, as illustrated in FIG. 15, i.e. when there is no fluid receptacle 4 within the pump body 2, or the fluid receptacle 4 is empty, then the retaining helical spring 58 is stretched and under tension.

The retaining helical spring 58 prevents the retaining member 31 from becoming trapped within the gaps of the spring or springs of the propulsion device, when the propulsion device is compressed. For example, when a fluid receptacle 4 is inserted into the infusion pump 1, the propulsion device is compressed and the retaining member 31 becomes slack. However, the tension in the surrounding retaining helical spring 58 is released such that the retaining helical spring 58 contracts and reverts to it unloaded natural length maintaining the slack retaining member 31 within its diameter.

The drive system then tensions the retaining member 31, such that the retaining member 31 exerts a tension force on the propulsion device, keeping the propulsion device in compression. By tensioning the retaining member 31 following insertion of a fluid receptacle 4 into the infusion pump 1, it is possible for the drive system to determine the amount of fluid in the fluid receptacle 4. According to one embodiment, the infusion pump 1 may be configured to sound an alarm if it is programmed to dispense more medicament than that provided in the fluid receptacle 4.

As stated above, the retaining member 31 together with the drive system exerts a tension force on the propulsion device, keeping the propulsion device in compression. The tension force may be released by actuation of the drive system in a controlled manner to regulate the delivery of the medicament.

Figure 9:
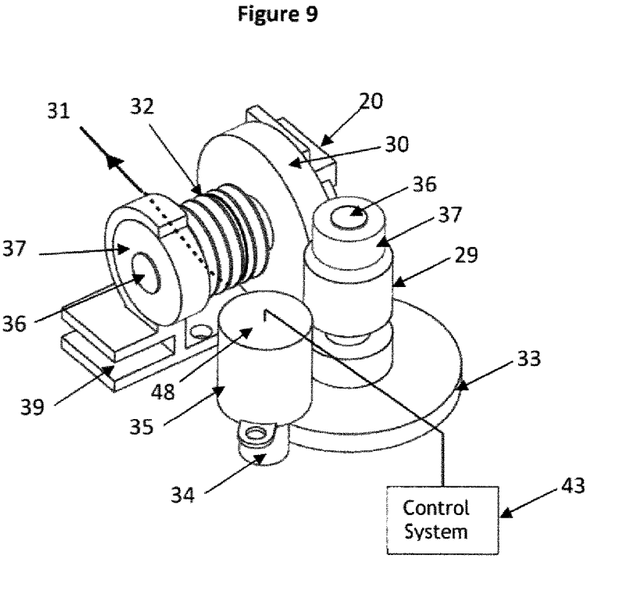
FIG. 9 illustrates an exemplary gearbox and drive system.
Figure 12:
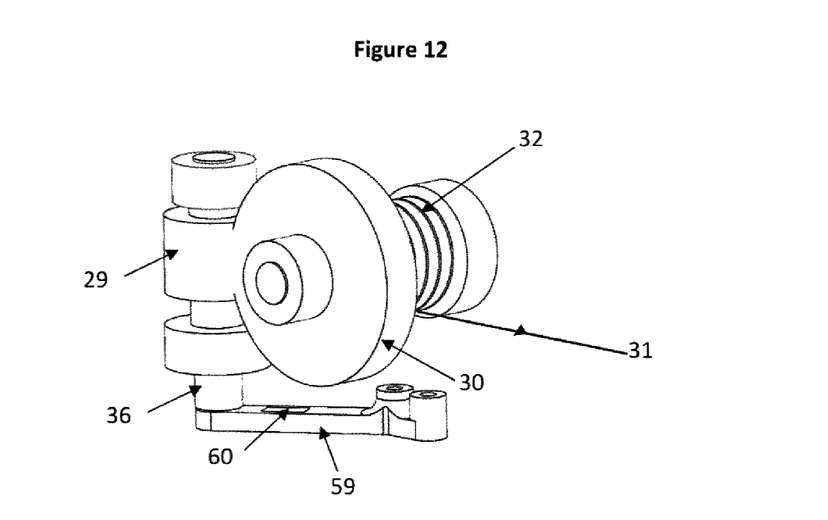
FIG. 12 illustrates part of the drive train and gearbox.

FIGS. 9 and 12 illustrates an exemplary drive system to which the retaining member 31 may be connected. The drive system may comprise a worm 29 and worm gear 30 connected to means to wind the retaining member 31 in a controlled manner around a spool 32. The number of full/partial winds around the spool indicating the volume of fluid in the receptacle 4.

The means to wind the retaining member 31 is preferably in the form of the inner diameter of a helical form and preferably a large toothed wheel 33 connected to the worm 29 and a small toothed wheel 34 or other means such as chains or belts for the purpose of reduction of rotary motion connected to a motor 35 with an associated rotary encoder 48 on the motor shaft. The drive system and associated shafts 36 and bearings 37 are contained in a structural framework commonly known as a gearbox 20.

Figure 16:
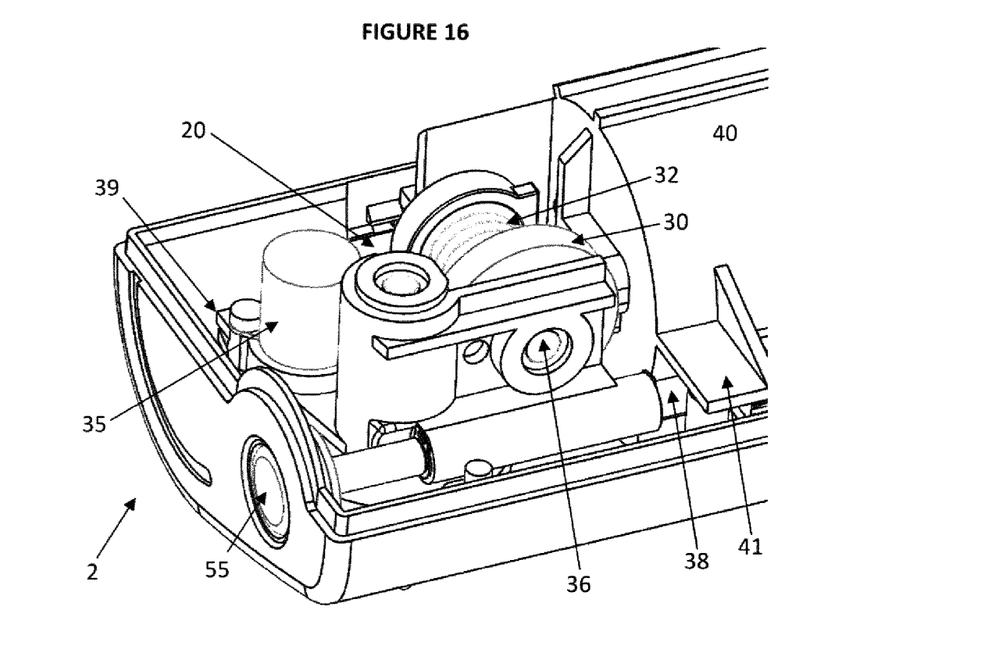
FIG. 16 illustrates a gearbox disposed within the pump body.

FIGS. 10 and 16 illustrates the gearbox 20 disposed within the pump body 2. The gearbox 20 may be supported and axially guided by the rigid member 38 of the infusion pump body 2. The gearbox 20 may be prevented from rotation about the axis of the rigid member 38 by guide features 39 residing on internal walls within the pump body 2, such as the internal chassis part 40.

According to another embodiment, the rigid member 38 may be acted upon and displaced axially by the worm 29 or a shaft 36 on which the worm 29 is placed. In a further embodiment, the rigid member 38 may be acted upon by the gearbox 20 or components it comprises and the gearbox 20 may be guided separately by features contained within the pump body 2 or upon the internal chassis part 40.

According to one embodiment, the chassis 40 comprises features 41 to guide the axial motion of the rigid member 38. The locking features 10 for engaging with the corresponding cap features 9 may also be provided on the chassis 40.

Figure 11:
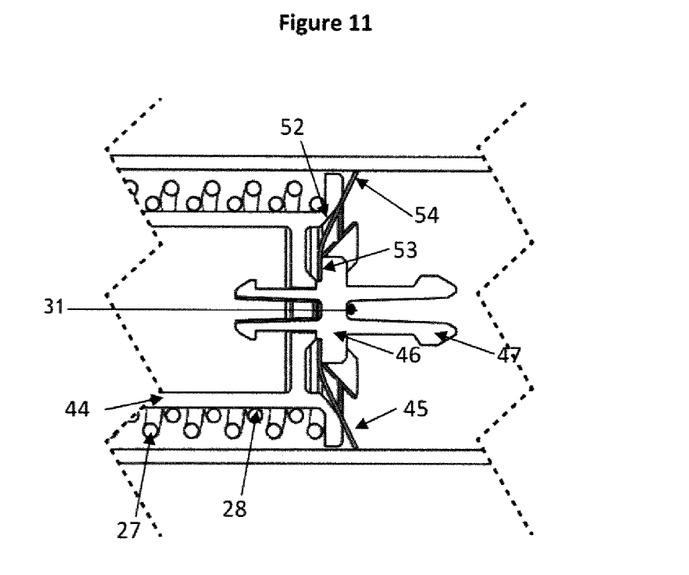
FIG. 11 illustrates a partial cross-sectional view of the spring support and brake parts.

Referring to FIG. 11, the retaining member 31 may be attached to an arrangement of brake parts 45, 46 provided at the support 44, the support 44 being provided at the moveable end of the propulsion device. When the propulsion device acts on the fluid receptacle 4 such that fluid is able to flow out of the receptacle 4, the force from the propulsion device creates tension force in the retaining member 31 which unless released by actuation of the motor 35 prevents the natural tendency of the propulsion device to extend in length. This tension acts through the retaining member 31 and upon the spool 32 to pull the connected gearbox 20 and rigid member 38 in an axial direction substantially parallel to the progression of the piston 7 through the fluid receptacle body 4a and towards and within the cap 3 such that when the cap 3 is connected to the pump body 2, the rigid member 38 acts upon the cooperating surface 22 of the moveable part of the pinch valve to move it against the lower forces of the valve spring 21 and away from occluding the tube 12 so as to permit the passage of fluid. Additionally, in this state the rigid member 38 extends from the pump body 2 and into the cap 3 in a manner to prevent the cap 3 from rotation and removal from the body 2, for example by the user. Furthermore, with reference to FIG. 8, during operation of the infusion pump 1, a catch feature 63 on the moveable part of the pinch valve and a ledge feature 49 on the lid 14 (illustrated in FIG. 6) prevents the user from opening the lid when infusion is in progress.

In a further embodiment, with reference to FIG. 10, the rigid member 38 may extend out of the body 2 to provide a user control surface 55 which can be displaced by the user to actuate the rigid member 38 and if the cap 3 is present to engage with the cap and interact with the cooperating surface 22 to open the pinch valve. During this displacement, the motor 35 may be actuated by the control system 43 to restore tension forces in the retaining member 31 and to retain the rigid member 38 in its displaced position.

The control system is configured the actuate the motor 35 of the drive system in a controlled manner to regulate the delivery of the medicament.

A further mechanical means may be provided to prevent the cap 3 from being rotated and removed from the pump body 2, for example by the user, during use. A sliding member 51 may be retained within the cap 3 but movable to extend into a corresponding cavity 42 in the pump body 2 in the manner of a door lock bolt such that in this extended position the cap 3 cannot be rotated and removed. Alternatively, the sliding member 51 may be retained within the pump body 2 but movable to extend into a corresponding cavity 42 in the cap 3. The sliding member 51 may comprise a detectable object such as an optical or mechanical surface or magnet such that in its extended state the detectable object can be detected by a sensor, such as an optical or electrical or magnetic switch in the pump body 2/cap 3 connected to the electronic control system 43 of the pump. The control system 43 may then determine if the sliding member 51 is in the extended or retracted state and only actuate the motor 35 to deliver medicament fluid when it is determined that the sliding member 51 projects into the corresponding cavity.

In another state of operation, when the retaining member 31 is not under tension, for instance when the fluid delivery has been stopped or the tube clamp 50 is occluding the tube 12, then the pinch valve spring 21 acts via the cooperating surface 22 to push the rigid member 38 towards the pump body 2 and away from the cap 3, such that the rigid member 38 no longer extends within the cap 3 and the cap 3 can be rotated and removed.

According to one embodiment, illustrated in FIG. 11, the support 44 provided at the moveable end of the propulsion device comprises a substantially circular periphery, a central hole and a partially concave surface 52. The support 44 around its periphery and on its partially concave or conical surface 52 contacts a braking member 45, the opposing side of the braking member 45 is in contact with a brake support part 46. The brake support part 46 comprises a partially convex or conical surface 53 which is tethered to the retaining member 31 extending through the braking member 45 and the spring support 44. The combination of force from the propulsion device and the opposing and reactionary tension force within the retaining member 31 acting through the spring support 44 and brake support part 46 deforms the braking member 45 into a curved or conical shape. When the braking member 45 is deformed, parts of its outer periphery 54 along a longer radial path are retracted away from contact with the interior walls of the fluid receptacle body 4a.

Should the retaining member 31 break/snap, the braking member 45 will return to its natural and substantial flatter shape and parts of its outer periphery 54 will engage the inner walls of the fluid receptacle body 4a in the manner of a brake and thereby prevent the propulsion device from indirectly advancing the piston 7 in the fluid receptacle body 4a and dispensing medicament fluid. In addition, should the retaining member 31 break, the tension acting through the retaining member 31 and upon the spool 32 to pull the connected gearbox 20 and rigid member 38 in an axial direction through the fluid receptacle body 4a and within the cap 3 is removed. Consequently, the rigid member 38 is moved in the opposite direction by the valve spring 21 and the pinch valve in the cap 3 is closed preventing the dispensing of medicament fluid. The infusion pump thus comprises several safety mechanisms in the event of retaining member 31 (cable) breakage.

The brake support part 46 is provided with a plurality of features such as clips 47 that engage with the seal support 6 within the fluid receptacle 4 for the purposes of resisting movement of the piston 7 if a negative pressure is applied to the fluid from the attached tube 12 as might occur if the tube is allowed to extend substantially downwards from the infusion pump. The geometry of the two sets of opposing surfaces of the clips 47 is such that the force to engage the brake support 46 with the seal support 6 is lower than the force to disengage. According to one embodiment, the force to disengage the brake support 46 from the seal support 6 is higher than the force created by the siphon vacuum of the fluid receptacle 4.

In addition, the engagement of the brake parts 45, 46 with the seal support 6 and the force required to disengage these during infusion ensures that a negative pressure resulting from a position of the tube entry to the patient appreciably lower than the infusion pump cannot result in disengagement which would otherwise allow fluid to siphon from the fluid receptacle in an unintended manner.

Figure 13:
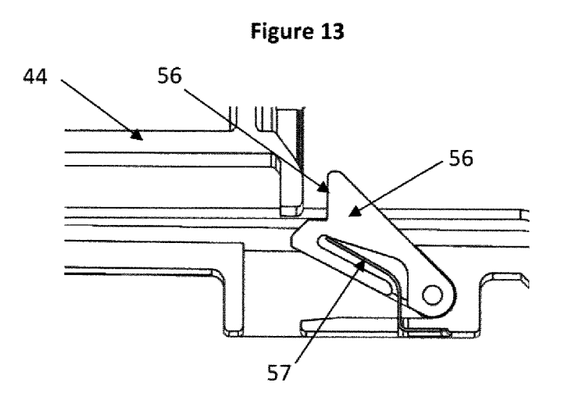
FIG. 13 illustrates a cross-sectional view of a stop bar and associated parts.

A pivoting and moveable stop bar 56, illustrated in FIG. 13, may be situated near to the limit of travel of the spring support 44. The stop bar 56 is supported by the pump body 2 or chassis 40 at an end that is pivotable and is acted upon by a spring or flexible lever 57 to move a surface distal from the pivoting end into the path of the spring support 44 such that if no fluid receptacle 4 is present the motion of the spring support 44 is prevented from continuing past the stop bar 56. The stop bar 56 is displaced from its rest position if a fluid receptacle 4 is placed into the pump so that it does not impede fluid delivery.

The control system 43 can use the position of the stop bar 56 when there is no fluid receptacle 4 present in combination with a reduced output from a sensing means 60, described below, to recognize the position of the spring support 44 in contact with the stop bar 56 to be equivalent to an emptied fluid receptacle 4. This position can be used as a start point from which the control system 43 can determine the volume of fluid in a fluid receptacle 4 inserted in to the pump body 2 by counting the motor 35 revolutions and fractions thereof from the encoder 48 needed to wind the slack retaining member 31 around the spool 32 and until tension forces are restored in the retaining member 31.

FIG. 12 illustrates the drive system within the gearbox 20 including a support region 59 to withstand the axial or thrust forces exerted on the worm 29 by the tension forces in the retaining member 31. Force or pressure sensing means 60 such as is provided by a strain gauge, force sensing resistor, load cell or pressure sensitive material may be placed either in between the worm 29 or the shaft 36 upon which it sits and the support region 59 to measure direct thrust or upon or within the support region 59 or an associated linkage to measure the strain or load imparted by the thrust force. Sensing of the magnitude of this thrust force can be used by the control system 43 to infer a reduction in the tension force in the retaining member 31 and further to infer an increase in pressure in the fluid 8 resulting from an occlusion in the tube 12 or the completion of delivery of the fluid 8. The force or pressure sensing means 60 may also detect the level of tension force within the retaining member 31. The level of tension force within the retaining member 31 can be used to detect a partial or complete cessation of the intended flow of medicament fluid, the completion of delivery and/or the insertion of a receptacle containing fluid.

Ambulatory infusion devices comprising a length of tubing between the pump and the patient infusion site can suffer from obstruction of the flow of medicament fluid through the tube caused by flattening or kinking of the tube, crystallization of drug compounds or closure of the patient vein known as an occlusion which causes a pressure increase in the fluid receptacle. It is advantageous to detect this occurrence at the earliest opportunity and to sound alarms at predetermined levels of increased pressure. The infusion pump described herein is able to detect an increase in pressure rapidly because of the direct nature of the forces within the propulsion device and retaining member and the low level of structural elasticity and hysteresis. In addition, if the sensor 60 were to detect a total loss of force, when not expected, it could infer failure of the retaining member 31 and can be used to sound an alarm.

Figure 2:
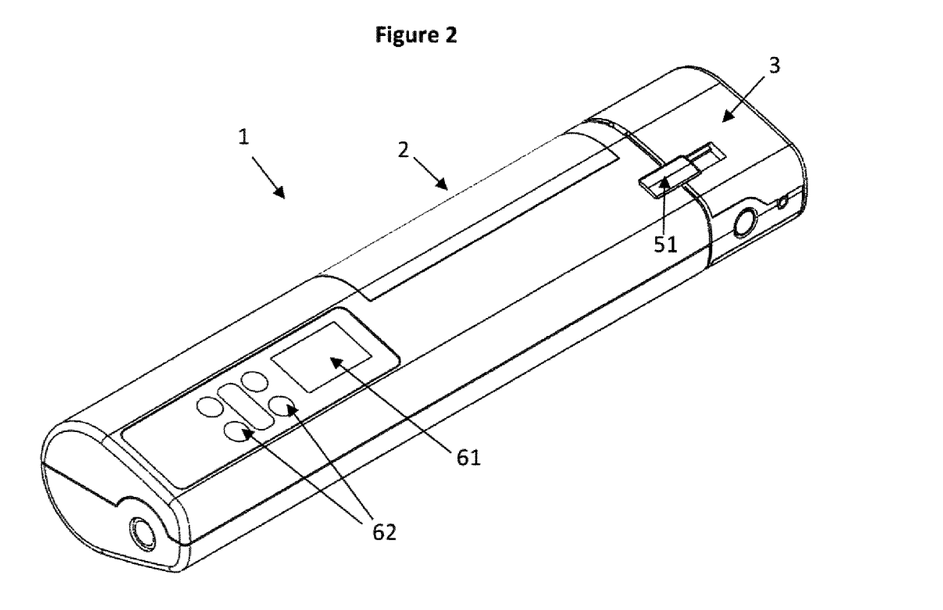
FIG. 2 illustrates an external view of an assembled infusion pump.

The body 2 may also comprise a user interface on its outer surface, illustrated in FIG. 2, that comprises a display 61 that is directed by the control system 43 and user operated switches 62 that are inputs to the control system. The user operated switches 62 may be disabled to prevent the user from changing the settings of the pump which together with means to prevent the opening and/or removal of the cap obviates with the need for a further enclosure to the pump also commonly known as a lockbox.

Those skilled in the art will appreciate that while the foregoing has described what is considered to be the best mode and where appropriate other modes of performing the invention, the invention should not be limited to the specific configurations and methods disclosed in this description of the preferred embodiment. Those skilled in the art will recognize that the invention has a broad range of applications, and that the embodiments may take a wide range of modifications without departing from the inventive concept as defined in the appended claims.

According to one aspect, an infusion pump intended for controlled administration of a fluid is provided. The infusion pump comprising: a receptacle for storing the fluid, the receptacle having an outlet connected to a tube to deliver the fluid, a piston arrangement in the receptacle and a handle removable from the piston arrangement; propulsion means to push the piston arrangement towards the outlet to deliver the fluid; retaining means which engage with the piston arrangement to control its position and movement towards the outlet of the receptacle; a normally closed valve acting upon the tube to prevent the passage of fluid through the tube; a rod actuated by tension forces in the retaining means to open the normally closed valve to allow the passage of fluid through the tube.

According to another aspect, an infusion pump intended for controlled administration of a fluid is provided. The infusion pump comprising: a receptacle for storing the fluid, the receptacle having an outlet connected to a tube to deliver the fluid, a piston arrangement in the receptacle and propulsion means to push the piston arrangement towards the outlet where the propulsion means comprises a plurality of concentrically arranged helical springs with adjacent springs having opposing directions of winding.

According to another aspect, the concentrically arranged helical springs are each longer than the length of the fluid receptacle and preferably by a factor exceeding 1.5 and their compressed length resulting from a fluid receptacle when full is longer than their coil-bound lengths by a factor of more than 1.1.

According to another aspect, the pump comprises a body and cap and the receptacle is retained by connection of the cap and body in the form of a rotating screw, bayonet or clip feature to prevent access to the fluid receptacle during delivery of the fluid.

According to another aspect, the gearbox contains a worm which resists the tension force of the retaining means and the rod is actuated by an axial motion of the worm or the gearbox or another part contained within the gearbox.

According to another aspect, the gearbox is supported upon the rod and both are further constrained to motion in a direction substantially parallel with the axis of the rod.

According to another aspect, the rod or part thereof is extended to an outer surface of the body and provides the user means to actuate the movement of the rod and thereby to open the valve if the cap is present.

According to another aspect, a force sensor used to detect the tension force within the retaining means is placed about the end of the worm or a shaft upon which is it mounted to measure the axial force upon the worm.

According to another aspect, the force sensor is placed within a part of the gearbox structure that is supporting the axial force from the end of the worm or a shaft upon which is it mounted.

According to another aspect, the cap comprises an engageable catch between the two outer parts to retain the parts in the closed position until the catch is disengaged by moving a user operable surface and which is prevented from disengagement when the engageable catch is actuated indirectly by the rod.

According to another aspect, a further catch between the two parts of the cap is engaged when directly or indirectly actuated by the rod to retain the parts in the closed position and is otherwise disengaged.

According to another aspect, the body substantially comprises a rod that when actuated by forces in the retaining means extends from a surface of the body in close cooperation with the cap and extends into the cap preventing the rotation and removal of the cap from the body.

According to another aspect, the cap comprises a sliding member that can be extended from a surface of the cap in close cooperation with the body and extended into a cavity on the body to prevent its removal.

According to another aspect, the sliding member contains an object the presence of which can be sensed so that the extended position of the sliding member from the cap into the body can be detected by the control system of the pump.

According to another aspect, the cap contains a spring element acting to close the valve also actuates the rod from its extended position towards the body allowing the removal from the body.

According to another aspect, the body comprises a moveable stop bar that prevents the extension of the propulsion means and associated parts upon contact if there is no fluid receptacle present within the body of the pump.

According to another aspect, the moveable stop bar is placed to prevent extension of the propulsion means and associated parts in the same position the propulsion means and associated parts occupy at the completion of fluid delivery from the fluid receptacle.

According to another aspect, an encoder fitted to the motor determines the fluid content of a receptacle inserted into the body by counting the motor revolutions and fractions thereof required to move the propulsion means and associated parts from the stop bar and until tension forces are restored in the retaining means.

According to another aspect, a user interface comprising a visual display and buttons that can be disabled to prevent the user from changing the settings of the pump which together with means to prevent the removal of the cap obviates with the need for a further enclosure to the pump also commonly known as a lockbox.

According to another aspect, the body comprises a chassis part that includes support for the immovable end of the means of propulsion and means to engage the cap.

According to another aspect, the fluid receptacle comprises a handle that is disengageable from the piston arrangement by rotation and includes a feature that requires a higher torque to be applied to overcome the feature before further and free rotation to remove the handle.

According to another aspect, a brake support part that is engageable to the seal arrangement by flexing members the unequal angles of whose cooperating surfaces provide a lower engagement force and a higher disengagement force.

According to one aspect, an infusion pump for controllably dispensing fluid is provided. The infusion pump comprising: an infusion pump body configured to receive a receptacle of fluid; and a cap configured to receive a tube coupled to the fluid receptacle for dispensing the fluid; the infusion pump body comprising: a propulsion device biased to propel fluid from the fluid receptacle into the tube; a retaining member coupled to the propulsion device; and a drive system coupled to the retaining member, wherein actuation of the drive system enables the propulsion device to controllably dispense the fluid; and wherein the propulsion device comprises a plurality of concentrically arranged helical springs, adjacent springs having opposing directions of winding.

According to another aspect, when a fluid receptacle is provided in the infusion pump body, the drive system is further configured to provide tension in the retaining member resulting in the rigid member projecting into the cap.

According to another aspect, the plurality of concentrically arranged helical springs comprises two concentrically arranged helical springs.

According to another aspect, the plurality of concentrically arranged helical springs are each longer in natural length than the length of the fluid receptacle by a factor greater than 1.5.

According to another aspect, when a full fluid receptacle is provided in the infusion pump body, the plurality of concentrically arranged helical springs are compressed, and the length available in the infusion pump body for the compressed plurality of concentrically arranged helical springs is longer than a coil-bound length of the plurality of concentrically arranged helical springs by a factor equal to or greater than 1.5.

According to another aspect, a fixed end of the propulsion device is coupled to the pump body and a moveable end of the propulsion device is biased to move away from the fixed end of the propulsion device.

According to another aspect, the retaining member is coupled to the moveable end of the propulsion device.

According to another aspect, the infusion pump further comprises: a retaining helical spring surrounding the retaining member.

According to another aspect, the retaining helical spring is coupled at a first end to the moveable end of the propulsion device and is coupled at a second end to the pump body.

According to another aspect, the retaining helical spring contracts to its natural length when a fluid receptacle is provided in the pump body.

According to another aspect, the retaining member extends through a center of the propulsion device.

According to another aspect, the retaining member comprises a plurality of retaining cables.

According to another aspect, the infusion pump further comprises a control system for controlling actuation of the drive system.

According to another aspect, one of the cap or the infusion pump body further comprises a sliding member configured to moveably project into a cooperating cavity provided in the other of the cap or the infusion pump body.

According to another aspect, the control system comprises a sensor configured to detect when the sliding member projects into the cooperating cavity.

According to another aspect, the infusion pump body further comprises a moveable stop bar configured to prevent the propulsion means projecting beyond the infusion pump body when no fluid receptacle is provided in the infusion pump body.

According to another aspect, the drive system comprises a motor and an encoder coupled to the motor, the encoder configured to determine a number of motor revolutions and fractions thereof required to provide tension in the retaining member when a fluid receptacle is provided in the infusion pump body.

According to another aspect, the infusion pump further comprises a braking member coupled to the moveable end of the propulsion device, the braking member configured to prevent the propulsion device from propelling fluid from the fluid receptacle into the tube when tension is removed from the retaining member.

According to another aspect, the pump body and the cap comprise corresponding locking features configured to retain a fluid receptacle within the pump body of the infusion pump.

According to another aspect, the drive system comprises a force sensor configured to measure tension force within the retaining member.

According to another aspect, the force sensor is provided about an end of a worm or on a shaft upon which the worm is mounted to measure axial force upon the worm gear.

According to another aspect, the force sensor is provided within a part that is supporting the axial force from the end of the worm or a shaft upon which the force sensor is mounted.

The invention claimed is:

1. An infusion pump for controllably dispensing a fluid, the infusion pump comprising:
    an infusion pump body configured to receive a receptacle of fluid; and
    a cap configured to receive a tube coupled to the fluid receptacle for dispensing the fluid, the cap comprising a valve configured to occlude the tube by pinching an exterior of the tube;
    the infusion pump body comprising:
        a propulsion device biased to propel the fluid from the fluid receptacle into the tube;
        a retaining member coupled to the propulsion device;
        a drive system coupled to the retaining member, wherein actuation of the drive system enables the propulsion device to controllably dispense the fluid; and
        a rigid member coupled to the drive system and configured to moveably project into the cap to open the valve to allow a passage of the fluid through the tube, wherein the valve is located outside a path of the fluid.

2. The infusion pump of claim 1, wherein the valve comprises a fixed valve part, a moveable valve part, and a biasing member configured to bias the moveable valve part towards the fixed valve part to occlude the tube.

3. The infusion pump of claim 2, wherein the rigid member is configured to displace the moveable valve part away from the fixed valve part when the rigid member projects into the cap to allow the passage of the fluid through the tube.

4. The infusion pump of claim 2, wherein the biasing member is configured to expel the rigid member from the cap when all of the fluid has been propelled from the fluid receptacle.

5. The infusion pump of claim 1, wherein the rigid member is configured to moveably project into the cap to prevent the cap from opening and/or to prevent removal of the cap from the infusion pump.

6. The infusion pump of claim 1, further comprising:
    a retaining helical spring surrounding the retaining member, wherein the retaining helical spring is coupled at a first end to the propulsion device and is coupled at a second end to the infusion pump body.

7. The infusion pump of claim 6, wherein the retaining helical spring is configured to contract to a natural length of the retaining helical spring when the fluid receptacle is inserted into the infusion pump body.

8. The infusion pump of claim 1, further comprising a control system for controlling actuation of the drive system.

9. The infusion pump of claim 8, wherein one of the cap or the infusion pump body further comprises a sliding member configured to moveably project into a cooperating cavity provided in the other of the cap or the infusion pump body, and wherein the control system comprises a sensor configured to detect when the sliding member projects into the cooperating cavity.

10. The infusion pump of claim 1, wherein the infusion pump body further comprises a moveable stop bar configured to prevent the propulsion device from projecting beyond the infusion pump body when no fluid receptacle is provided in the infusion pump body.

11. The infusion pump of claim 1, wherein when the fluid receptacle is provided in the infusion pump body, the drive system is further configured to provide tension in the retaining member enabling the rigid member to project into the cap.

12. The infusion pump of claim 11, wherein the drive system comprises a motor and an encoder coupled to the motor, the encoder configured to determine a number of motor revolutions and/or fractions thereof required to provide the tension in the retaining member when the fluid receptacle is provided in the infusion pump body.

13. The infusion pump of claim 12, wherein the drive system comprises a force sensor configured to measure the tension in the retaining member.

14. The infusion pump of claim 13, wherein the drive system comprises a worm mounted on a shaft, and wherein the force sensor is provided at an end of the worm or on the shaft to measure an axial force upon the worm, and wherein the force sensor is provided within a part that is supporting the axial force from the end of the worm or the shaft.

15. The infusion pump of claim 11, further comprising a braking member coupled to a moveable end of the propulsion device and the retaining member, the braking member configured to prevent the propulsion device from propelling the fluid from the fluid receptacle into the tube when the tension is removed from the retaining member.

16. The infusion pump of claim 15, wherein the braking member comprises flexing members configured to engage the fluid receptacle, wherein the flexing members provide a lower engagement force and a higher disengagement force relative to one another, wherein a force required to disengage the flexing members from the fluid receptacle is higher than a force required to engage the flexing members with the fluid receptacle.

17. The infusion pump of claim 1, wherein the propulsion device comprises two or more concentrically arranged helical springs, adjacent springs having opposing directions of winding, and wherein the two or more concentrically arranged helical springs are each longer in natural length than a length of the fluid receptacle by a factor equal to or greater than 1.5.

18. The infusion pump of claim 17, wherein when a full fluid receptacle is provided in the infusion pump body, the two or more concentrically arranged helical springs are compressed, and a length available in the infusion pump body for the compressed two or more concentrically arranged helical springs is longer than a coil-bound length of the two or more concentrically arranged helical springs by a factor equal to or greater than 1.1.

19. The infusion pump of claim 1, wherein a fixed end of the propulsion device is coupled to the infusion pump body and a moveable end of the propulsion device is biased to move away from the fixed end of the propulsion device.

20. The infusion pump of claim 1, wherein the infusion pump body is configured to receive the fluid receptacle comprising connection features for connection to opposing connection features of a disengageable handle, wherein the connection features require the handle or fluid receptacle to be rotated with a higher torque, than required to engage the handle to the fluid receptacle, so as to overcome the connection features and remove the handle.

* * * * *